(12) United States Patent
Atanassov et al.

(10) Patent No.: US 9,742,011 B2
(45) Date of Patent: Aug. 22, 2017

(54) TETHERING OF CONFACTORS ON GRAPHENE-LIKE MATERIALS

(71) Applicants: Plamen B Atanassov, Santa Fe, NM (US); Claudia W Narvaez Villarrubia, Tijeras, NM (US); Sergio Omar Garcia, Los Lunas, NM (US)

(72) Inventors: Plamen B Atanassov, Santa Fe, NM (US); Claudia W Narvaez Villarrubia, Tijeras, NM (US); Sergio Omar Garcia, Los Lunas, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/776,777

(22) PCT Filed: Mar. 17, 2014

(86) PCT No.: PCT/US2014/030130
§ 371 (c)(1),
(2) Date: Sep. 15, 2015

(87) PCT Pub. No.: WO2014/145377
PCT Pub. Date: Sep. 18, 2014

(65) Prior Publication Data
US 2016/0036061 A1 Feb. 4, 2016

Related U.S. Application Data

(60) Provisional application No. 61/786,333, filed on Mar. 15, 2013.

(51) Int. Cl.
*C07H 19/207* (2006.01)
*C12N 11/02* (2006.01)
*C12N 11/06* (2006.01)
*C12P 19/36* (2006.01)
*H01M 4/90* (2006.01)
*H01M 4/86* (2006.01)
*H01M 8/16* (2006.01)
*C01B 31/02* (2006.01)

(52) U.S. Cl.
CPC ....... *H01M 4/9008* (2013.01); *C01B 31/0253* (2013.01); *C07H 19/207* (2013.01); *C12N 11/02* (2013.01); *C12N 11/06* (2013.01); *C12P 19/36* (2013.01); *C01B 2202/06* (2013.01); *H01M 4/90* (2013.01); *H01M 8/16* (2013.01); *H01M 2004/8684* (2013.01); *Y02E 60/527* (2013.01)

(58) Field of Classification Search
CPC ............ C01B 31/0253; C01B 2202/06; C07H 19/207; C12N 11/02; C12N 11/06; C12P 19/36; H01M 4/9008; H01M 2004/8684; H01M 4/90; H01M 8/16; Y02E 60/50
See application file for complete search history.

*Primary Examiner* — Paul A Zucker
*Assistant Examiner* — Mark Luderer
(74) *Attorney, Agent, or Firm* — Gonzales Patent Services; Ellen M. Gonzales

(57) ABSTRACT

A family of customizable tethering molecules for tethering cofactors such as, but not necessarily limited to, nicotinamine adenine dinucleotide (NAD+/NADH, NAD(P)+/NAD(P)H) to substrates or structures formed from or including graphene-like materials is described. The tethered cofactor can then be used, for example, as biosensors employed for clinical diagnostic, food industry, medical drug development and environmental and military applications, as well as in reagentless biofuel cells for power generation.

9 Claims, 6 Drawing Sheets

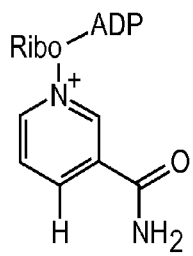
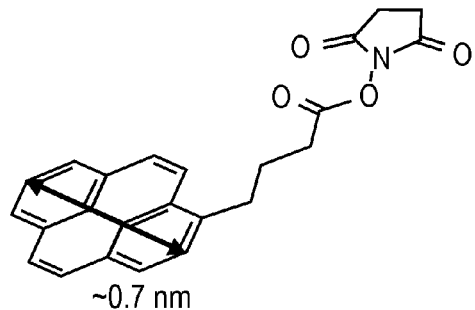
FIG. 1  FIG. 2
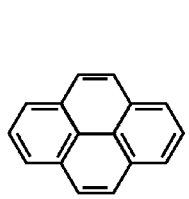 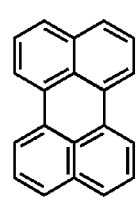 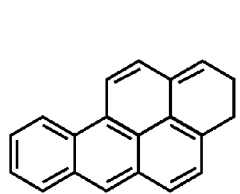 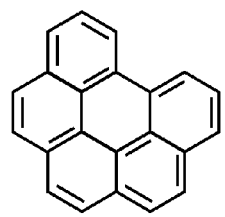
Pyrene  Pyrelene  Benzo[a]pyrene  Benzo[*ghi*]pyrene
FIG. 3  FIG. 4  FIG. 5  FIG. 6
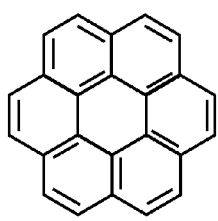 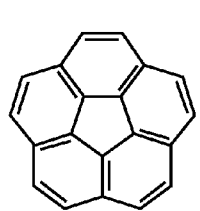 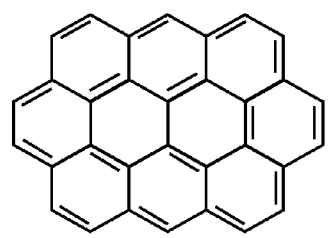
Corene  Corannulene  Ovalene
FIG. 7  FIG. 8  FIG. 9
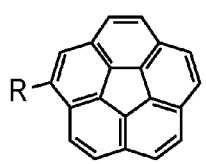 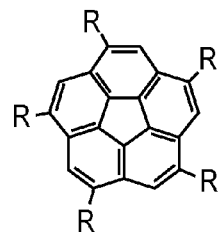
FIG. 10  FIG. 11

TETHERING OF CONFACTORS ON GRAPHENE-LIKE MATERIALS

CROSS-REFERENCE TO RELATED APPLICATIONS

The following application claims benefit of U.S. Provisional Application No. 61/786,333 titled "Adenine Nicotinamine Dinucleotide (Phosphate) Tethered by Alkyl-Ester Cyclic-Aromatic-Hydrocarbons Footprint Molecular Structures on Multi-walled Carbon Nanotubes" and filed Mar. 15, 2013, which is hereby incorporated by reference in its entirety.

BACKGROUND

Cofactors are non-protein chemical compounds that are required by a protein, most commonly an enzyme, to perform a biological activity. Accordingly, man-made systems that are intended to replicate certain biological functions, such as enzymatic activity, require the presence of these cofactors in a way in which they are made available to the proteins in the system in a controlled manner. A common way to control the manner in which a biological, such as a cofactor, is presented and used in a system is by immobilizing the biological to a substrate. This enables the system to guarantee presence of the biological and to control both the location and concentration (if desired) of the biological. Some methods of immobilization can even go so far as to control the position or orientation of a given biological.

However, immobilization of particular biologicals can present problems. First, some systems may require a particular type of substrate or require a substrate formed from a particular type of material that is not necessarily friendly to certain traditional attachment mechanisms. For example, graphene-like materials, which are often used or required in energy-production systems such as fuel cells, do not easily avail themselves to the use of attachment chemistries that rely on the presence of covalent bonds. Moreover, the biological itself may present certain challenges. For example, dynamic cofactors interact with multiple proteins in sequence and thus may require a certain degree of freedom in order to operate.

An exemplary dynamic cofactor is nicotinamine adenine dinucleotide (phosphate) ($NAD^+(P)/NAD(P)H$). The structure of $NAD^+/NADH$ (without phosphate group) is shown in FIG. 1. $NAD^+/NADH$ is found in all living cells and serves two important functions. First, it is involved in redox reactions, enabling metabolism by trading electrons with other molecules as it alternates between its NAD and NADH forms. Second, it is used in many cellular processes including, acting as a substrate of enzymes that add or remove chemical groups from proteins in posttranslational modifications. Due to these important functions, is an important and highly interesting compound for both research and commercial applications.

Many of these applications, such as, for example, biofuel applications in which anodic enzymes require the presence of $NAD(P)^+/NAD(P)H$ as a cofactor for catalysis, would benefit from the ability to immobilize or tether $NAD(P)^+/NAD(P)H$ to a substrate, and in particular, the ability to tether $NAD(P)^+/NAD(P)H$ to graphene-like structures such as multi-walled carbon nanotubes, single walled carbon nanotubes, graphene, rGO, and other graphene-based or graphene-containing substrates. However, the tethering of $NAD(P)^+/NAD(P)H$ has heretofore proven to be difficult, as $NAD(P)^+/NAD(P)H$ requires a certain degree of freedom of movement in order to function and thus previous methods that relied on simply immobilizing $NAD(P)^+/NAD(P)H$ directly to the surface of the substrate proved to be either of limited value or entirely unworkable.

Accordingly, there is a need for methodologies and chemistries for linking or tethering cofactors such as, but not necessarily limited to $NAD(P)^+/NAD(P)H$, to a substrate, and particularly a graphene-like substrate, that enable suitable immobilization of the cofactors without unduly inhibiting their ability to perform their desired biological function.

SUMMARY

According to an embodiment, a family of customizable linking molecules for tethering cofactors such as, but not necessarily limited to, nicotinamine adenine dinucleotide or nicotinamine adenine dinucleotide phosphate ($NAD^+/NADH$, $NADP^+/NADPH$) to substrates or structures formed from or including graphene-like materials is described. The tethered cofactor can then be used, for example, as biosensors employed for clinical diagnostic, food industry, medical drug development and environmental and military applications, as well as in reagentless biofuel cells for power generation.

BRIEF DESCRIPTION OF THE DRAWINGS

FIG. 1 depicts the chemical structure of nicotinamine adenine dinucleotide ($NAD^+$).

FIG. 2 depicts the chemical structure of pyrene butanoic acid succinimidyl ester (PBSE).

FIG. 3 depicts the chemical structure of pyrene.

FIG. 4 depicts the chemical structure of pyrelene.

FIG. 5 depicts the chemical structure of benzo(a)pyrene.

FIG. 6 depicts the chemical structure of benzo(ghi)pyrene.

FIG. 7 depicts the chemical structure of corene.

FIG. 8 depicts the chemical structure of corannulene.

FIG. 9 depicts the chemical structure of ovalene.

FIG. 10 depicts the chemical structure of a corannulene ring is shown with a mono(tert)-substituted butyl group.

FIG. 11 depicts the chemical structure of a corannulene ring is shown with a penta-(tert) substituted butyl group.

DETAILED DESCRIPTION

Figure 12:
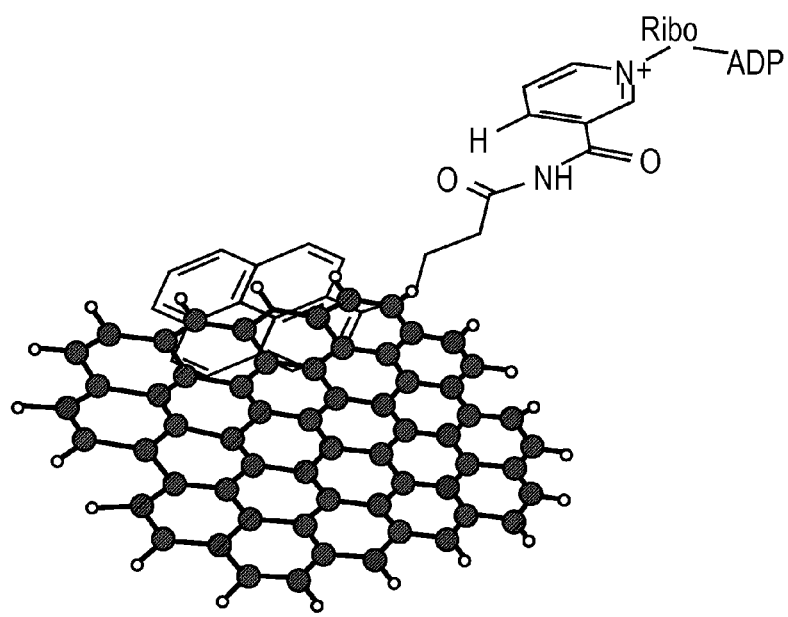
FIG. 12 depicts the tethering of the NAD molecule of FIG. 1 to the surface of a multi-walled carbon nanotube (MWCNT) via the PBSE tether molecule of FIG. 2.

In general, the present disclosure provides a family of customizable tethering molecules for tethering cofactors including, but not necessarily limited to, nicotinamine adenine dinucleotide (phosphate) (NAD+/NADH, NAD(P)+/NAD(P)H), pyrroloquinoline quinone (PQQ), flavin adenine dinucleotide (FAD), coenzyme A (CoA), thiamine, pyridoxine, vitamin B6 and vitamin B12 to graphene-like structures including, but not necessarily limited to, multi-walled carbon nanotubes (MWCNTs or MWNTs), single walled carbon nanotubes (SWCNTs or SWNTs), graphene, rGO, and other carbon-based or carbon-containing substrates.

According an embodiment, the tethering molecule comprises at least two parts: a polycyclic aromatic or polyarene "foot" at one end; and an ester moiety-containing alkyl-chain at the opposite "head" end. As interesting feature of the disclosed molecules, which enables them to act as a tethering molecule between the cofactors and graphene-like substrates described herein, is that the tethering molecules are able to engage in a non-covalent π-π interaction at the foot end and in a covalent interaction at the head. An exemplary compound having this structure is pyrene butanoic acid succinimidyl ester (PBSE) which is shown in FIG. 2.

Suitable aromatic or polyarene structures for use in linking molecule include, but are not necessarily limited to, the fused benzene structure in PBSE as shown in FIG. 2, pyrene (shown in FIG. 3), pyrelene (FIG. 4), benzo(a)pyrene (FIG. 5), benzo(ghi)pyrene (FIG. 6), corene (FIG. 7), corannulene (FIG. 8), ovalene (FIG. 9), and other molecular-benzene-based structures, cyclic aromatic hydrocarbons, or any graphene-like structures.

According to some embodiments, it may be desirable to optimize the interaction between the selected substrate and the tethering molecule. Accordingly one could vary the size of the foot of the tethering molecules, by, for example, selecting a desired one of the above-mentioned molecular-benzene-based structures in order to vary the strength of the π-π interaction. Simply put, a larger 'foot' with a chirality or molecular symmetry that confers a planar shape would have more surface area available for π-π interactions with the substrate, while a smaller foot would do the opposite. Accordingly, larger molecular structures allow for a stronger interaction with planar graphene-like structures while a smaller foot surface allows π-π interactions with substrates having a certain curvature on the surface, such as, for example, single walled carbon nanotubes (SWNTs). Moreover, by increasing the strength of the π-π interactions, increasing the foot size, the length of the alkyl group could be increased and the stability of the interaction will allow dynamics of the tethered cofactor, as described below to assure attachment of the tether to the graphene-like substrate surface Accordingly, as stated above, the alkyl chain can also be modified. For example, the length of the "arm" of the alkyl group can be designed to optimize the dynamics of the tethered cofactor in order to enable sufficient movement and interaction with the enzyme or other molecules, compounds, components, etc. with which the cofactor is intended to interact. Examples are shown in FIG. 10, where a corannulene ring is shown with a mono(tert)-substituted butyl group (R=butyl), and FIG. 11 where a corannulene ring is shown with a penta-(tert) substituted butyl group. The butyl group can then be treated for example, by employing monooxygenases and alcohol dehydrogenases to produce subterminal oxidation of the alkyl to alcohol, posterior oxidation to ketone and final oxidation to produce an ester moiety that will form an amide by reacting with the primary amine of the cofactor (or primary and secondary amine in an enzyme.) It will be understood that similar substitutions could be made in any of the ring structures disclosed herein. Of course those of skill in the art will be familiar with a wide variety of additional substitutions that could be made to obtain alkyl groups of the desired length.

According to another embodiment, the present disclosure provides a cofactor, such as, but not necessarily limited to NAD+, NADH, NAD(P)+, NAD(P)H, PQQ, FAD, coenzyme A (CoA), thiamine, pyridoxine, vitamin B6 and vitamin B12 tethered to a graphene-like substrate via a tether molecule, such as that described above. For the purposes of the present disclosure, the term "graphene-like" is used to mean fused-hexagonal rings with sp$^2$ electronic conformation distributed on a planar surface or in a cylindrical structure formed by a rolled sheet of the fused-hexagonal sp$^2$ conformation. For the sake of simplicity, the abbreviation "NAD(P)+/NAD(P)H" should be interpreted to include all other variants of the nicotinamine adenine dinucleotide family including NAD+, NADH, NAD(P)+ and NAD(P)H.

FIG. 12 depicts an exemplary embodiment wherein the NAD+ molecule of FIG. 1 is tethered to the surface of a multi-walled carbon nanotube (MWCNT) via the PBSE linker molecule of FIG. 2. When used as a tether, the linking molecule's foot interacts with the graphene-like structure (depicted in FIG. 12 as MWNT rings) via π-π stacking while the alkyl-ester in the linking molecule reacts with the amine group of the cofactor to form an amide or ester group, depending on the particular cofactor used. In embodiments wherein the cofactor is $NAD^+$, NADH, $NAD(P)^+$, NAD(P)H, PQQ, FAD, coenzyme A (CoA) or thiamine, the bond formed will result in an amide group since the ester will react with an amine (primary amine). Conversely, in embodiments where the cofactor is pyridoxine, vitamin B6 or vitamin B12, the reaction would generate another ester group since the reaction occurs between an ester and an alcohol group.

Regardless of the specific chemical reaction that forms the covalent bond between the cofactor and the tether, it can be seen from viewing FIG. 12 that this configuration provides a significant degree of freedom for the tethered cofactor such that is able to engage and interact with other molecules or compounds. As explained above, this freedom is of particular importance for dynamic cofactors such as $NAD(P)+/NAD(P)H$ molecules which are unique in that unlike other cofactors such as PQQ and FAD which permanently associate with an enzyme once they engage it, dynamic cofactors are able to repeated associate and disassociate with the same or different enzymes. Understandably, this ability to repeatedly associate and disassociate can, however, be hindered if the cofactor is not provided with enough freedom of movement. For example, $NAD(P)+/NAD(P)H$ molecules that are bound to the surface of a substrate may not be able to properly orient to interact with an enzyme and/or may not be able to find other partners with whom to interact.

In practice, $NAD(P)+/NAD(P)H$ molecules can be tethered to a substrate by mixing dissolved tether molecules and $NAD(P)+/NAD(P)H$ molecules, preferably at a molar ratio of around 1:1 under sufficient conditions to enable formation of an amide group between the tether and the $NAD(P)+/NAD(P)H$ molecule and then depositing the bound molecules on the substrate under sufficient conditions to enable π-π stacking between the tether and the substrate. Alternatively, one could deposit the tether structure on the substrate graphene-like structure and then add the dissolved cofactor to the substrate-tether surface to allow the formation of the amide group by reaction of the ester-moiety of the tether and the amine of the cofactor (or ester and alcohol group). The products not attached to the surface could then be removed by rinsing with water or phosphate buffer in both cases.

It will be understood that, while not specifically depicted, the same π-π stacking interaction can be used to attach the tethering molecule to other graphene-like structures including, but not limited to single walled carbon nanotubes (SWCNTs or SWNTs), graphene, rGO, and other carbon-based or carbon-containing substrates.

The tethering molecules and tethered cofactors described herein can be used, for example, in a wide variety of cofactor-dependent systems including, but not limited to $NAD(P)+/NAD(P)H$-dependent enzymes. Suitable systems include biosensors employed for clinical diagnostic, food industry, medical drug development and environmental and military applications, as well as reagentless biofuel cells for power generation. Biosensors that make use of both redox and non-redox processes can benefit from the inclusion of cofactors tethered on graphene-like substrates. Oxidation/reduction processes involving $NAD(P)+/NAD(P)H$ cofactors can be used for the development of electrochemical biosensors. Non-limiting examples of electrochemical biosensors include glucose, lactate, ethanol and malate biosensors that can employ $NAD(P)+/NAD(P)H$-dependent enzymes such as glucose dehydrogenase, lactate dehydrogenase, alcohol dehydrogenase and malate dehydrogenase, respectively, which are commonly used in both the clinical diagnostic and food industries. Similarly, ammonia biosensors (which measure production via urease) can be designed to utilize NADH-dependent glutamic dehydrogenase.

Furthermore, non-redox processes utilizing tethered cofactors as described herein can be employed in fluorescent biosensor and assay development. Drug development involving $NAD^+$/NADH enzymatic mechanisms such as the metabolism regulated by suirtins, poly(ADP-ribose) and polymerases (PARPs), and cyclic ADP-ribose synthases could employ also the tethered cofactor system on graphene-like structures.

Moreover, because the tethered $NAD(P)^+$/NAD(P)H cofactors can be used repeatedly, the disclosed embodiments can help minimize the cost of production and/or synthesis of pharmacological compounds where those processes require or utilize $NAD(P)+/NAD(P)H$-cofactors.

Figure 13:
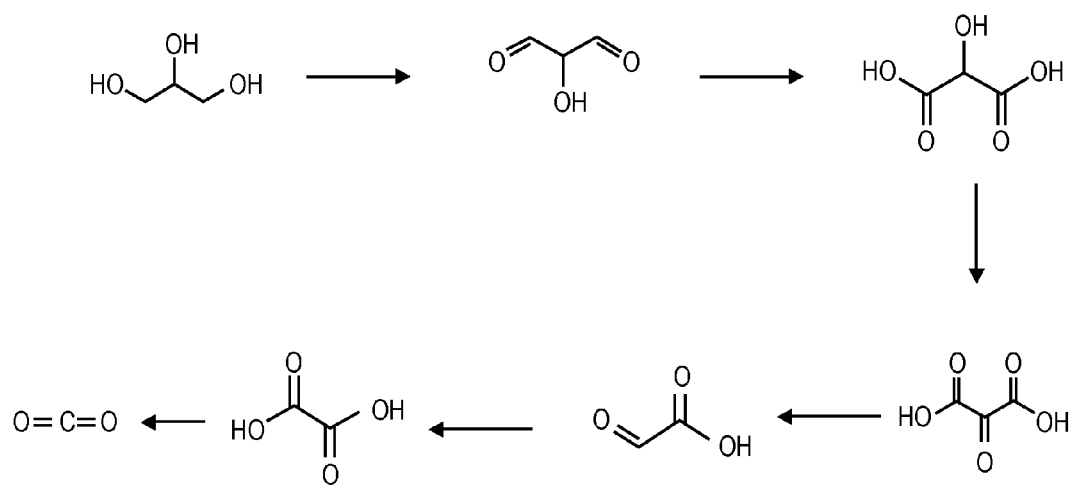
FIG. 13 shows the chemical processes involved in the glycerol oxidation cascade involving alcohol dehydrogenase (ADH), aldehyde dehydrogenase (AldDH) and oxaloacetate oxidase (OxOx) enzymes.

In the field of biofuel cell development for power generation for small devices for portable and implantable biomedical applications, a reagentless and friendly user design is highly desired. Enzymatic biofuel cells employing $NAD(P)^+$/NAD(P)H-dependent enzymes such as glucose dehydrogenase and alcohol dehydrogenase powered by glucose and ethanol (and/or glycerol) can integrate the tethering procedure for the cofactor. Furthermore, the invention can be utilized in enzymatic cascade systems for complete oxidation of a biofuel such as, for example, glycerol oxidation. As shown in FIG. 13, the glycerol oxidation cascade includes alcohol dehydrogenase (ADH), aldehyde dehydrogenase (AldDH) and oxaloacetate oxidase (OxOx) enzymes that undergo various consecutive steps to complete oxidation of glycerol to carbon dioxide and water. The cascade for glycerol oxidation needs to integrate both $NAD^+$/NADH-dependent enzymes and enzymatic systems that are not $NAD^+$/NADH-dependent enzymes such as oxalate oxidase enzyme (OxOx). During the cascade, OxOx is part of two steps that involve decarboxylation (by generation of $CO_2$, cascade of glycerol oxidation). The first reaction where OxOx is involved gives a product that will be used by AldDH. The second reaction where OxOx is involved finalizes the glycerol oxidation giving $CO_2$ as the final product. Both reactions are processes of electron transfer that will contribute to the overall current generation of the bioanode.

It will be appreciated that in some cases it may be desirable to tether both the cofactors and the enzymes to the same substrate. Examples of tethering agents that can be used for enzymes include, but are not limited to PBSE. In this case, the tethering would enable or even encourage the dynamic of the interaction between the enzyme and its cofactor by decreasing the distance between them and thus enhancing the interaction of both the enzyme and the cofactor. As mentioned previously, the length of the arm and foot of the tether-molecular structure can be design to accomplish the freedom for the dynamics of the processes on the substrate.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a catalyst" includes a plurality of such catalysts, and so forth.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Additional information may be gathered from the Examples section below.

EXAMPLES

I. Tethering of NAD+ to MWCNTs-Based Buckeye Paper

The electrode material, a MWCNTs-based buckeye paper, was initially washed with isopropanol (IPA) 30 and then with water. The PBSE tether was dissolved in dimethyl sulfoxide (DMSO) and the NAD+/NADH cofactor was dissolved in phosphate buffer (PB) 0.1M of pH 7.5. PBSE and NAD+/NADH were mixed in proper amounts to maintain a 1:1 molar ratio. Accordingly, for buckeye paper having a surface area of 3.7 $cm^2$, 5 mg NAD+/NADH was dissolved in 100 µl PB 0.1M, pH 7.5 and 2.9 mg PBSE in 100 µl DMSO. The dissolved NAD+/NADH and PBSE were mixed and deposited on the buckeye paper's surface.

II. Glycerol Oxidation Using NAD(P)+/NAD(P)H-Cofactor Tethered to MWCNT's Based Buckeye Paper (BEP) and CMN Grade Bucky Paper NAD(P)+/NAD(P)H-cofactor was tethered to MWCNTs-based buckeye paper having thickness of 15-250 µm and purity of ~100% MWNTs and CMN grade-bucky paper of 15-250 µm and a purity of ~100% (CMN) obtained from Buckeye Composite, Inc., using a PBSE tether and the procedures described above. ADH (3 mg), AldhDH (15 mg) and OxOx (1.25 mg) enzymatic systems were also immobilized to the substrates by entrapment in a carbon nanotube and chitosan polymeric matrix. The measurements of open circuit voltage, cyclic voltammetries as well as potentiostatic chronoamperommetries to develop polarization curves were performed. The results are shown in FIGS. 14-21.

Figure 14:
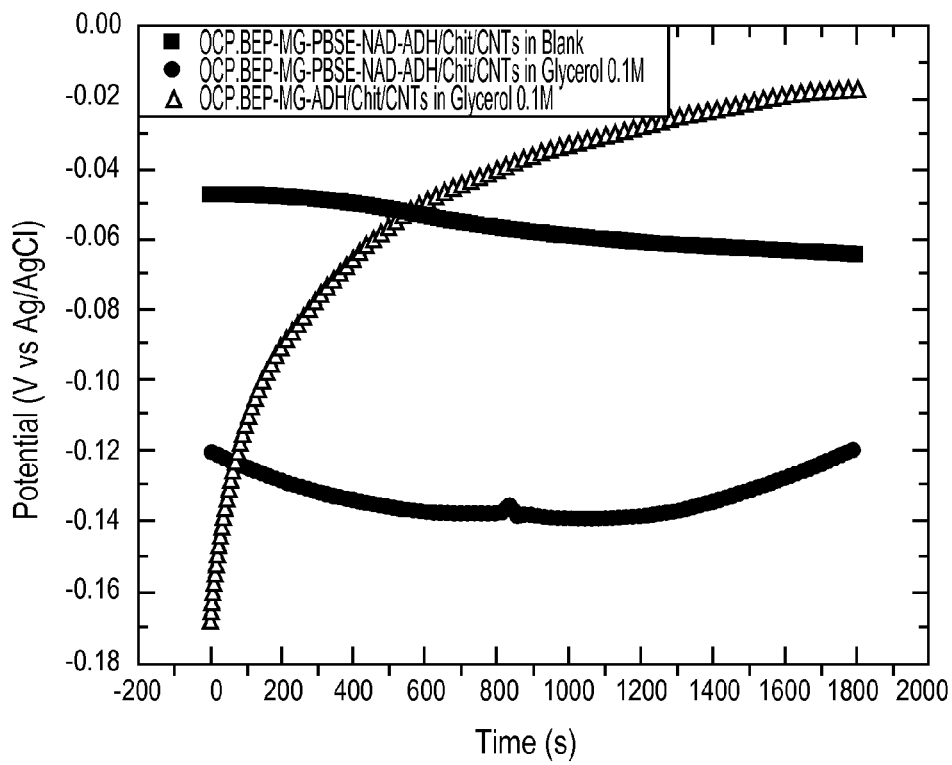
FIG. 14 is a graph showing the open circuit potential (OCP) of alcohol dehydrogenase (ADH)-based bioanodes with NAD tethered in blank solution (black curve) and glycerol 0.1M solution (red curve) [blank solution: 0.1M KCl in 0.1M phosphate buffer, pH 7.5] and NAD in solution with glycerol (blue curve) [solution: 0.1M glycerol, 1 mM $NAD^+$, KCl 0.1M in 0.1M phosphate buffer, pH 7.5].
Figure 15:
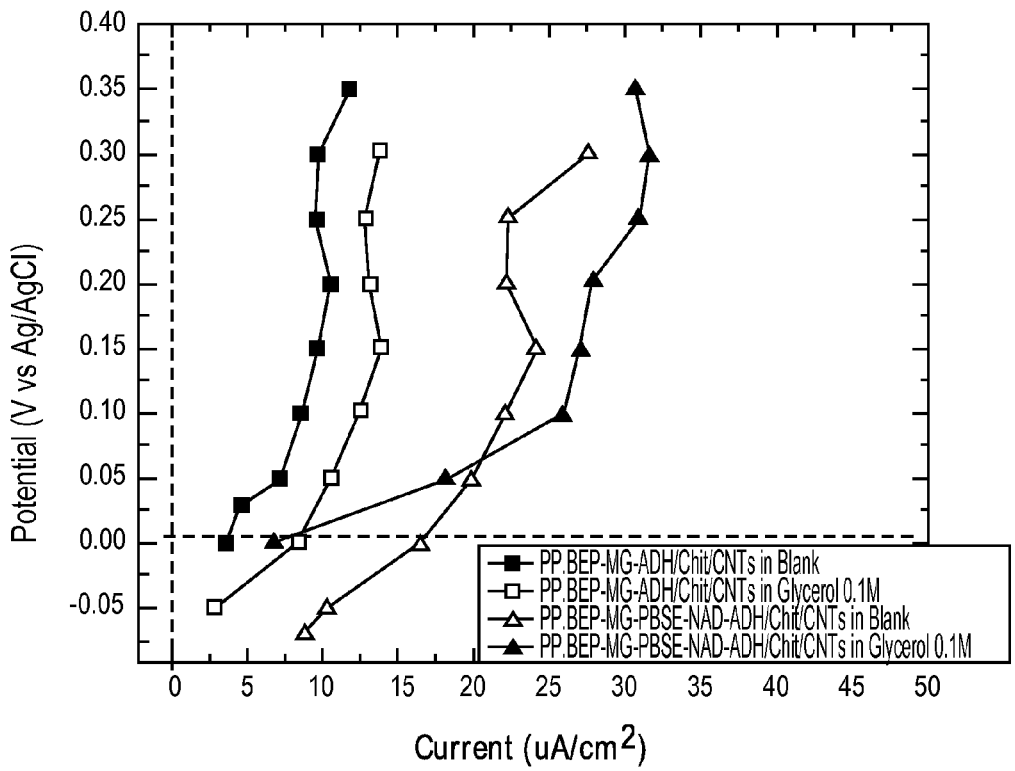
FIG. 15 is a graph of potentiostatic polarization curves, current density as a function of potential, for bioanodes employing ADH with NAD in solution in absence (┄┄) and presence of glycerol (-✻-) [blank solution: 1 mM $NAD^+$, 0.1M KCl in 0.1M phosphate buffer, pH 7.5] and $NAD^+$-tethered, also, in absence (-▲-) and presence of glycerol 0.1M (-▲-) [blank: 0.1M KCl in phosphate buffer, pH7.5, glycerol solution: 0.1M glycerol added to blank solution].

As demonstrated by the results in FIG. 14, thermodynamically, the system with $NAD^+/NADH$ tethered on the electrode has improved open circuit potential over the system with $NAD^+/NADH$ in solution ($OCP_{Tethered\ NAD+/NADH} < OCP_{NAD+/NADH\ solution}$). Turning to FIG. 15, the electrode with $NAD^+/NADH$ tethered shows improved current density generation for the $1^{st}$ step of glycerol oxidation compared to the system with $NAD^+/NADH$ in solution. There are other oxidation processes involved in the system and curves in blank ( ) also high current density compared to $NAD^+/NADH$ in solution. The kinetics of the $NAD^+$ tethered systems is slower than the anode with NAD in solution for low potentials and current density ( ). Above 50 mV, the tethered $NAD^+$-system shows better performance for current generation ( ) approximately 25 µA/$cm^2$ at 0.1V compared to ~12.5 µA/$cm^2$ for $NAD^+/NADH$ in solution at the same potential.

Figure 16:
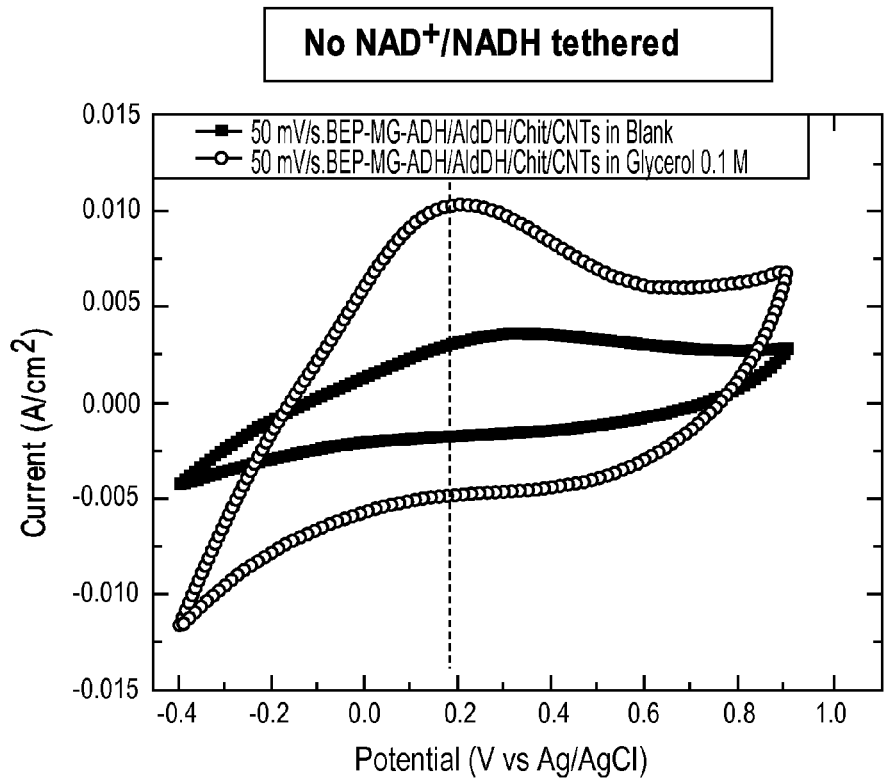
FIG. 16 is a graph of cyclic voltammograms of ADH and AldDH-based anodes with NAD+/NADH in solution in absence of glycerol, blank solution, (black curve) [blank solution: 1 mM NAD+, 0.1M KCl in 0.1M phosphate buffer, pH 7.5] and in presence of glycerol ([solution: 0.1M glycerol, 1 mM NAD+, 0.1M KCl in 0.1M phosphate buffer, pH 7.5]) where the oxidation peak is at approximately 0.2V and 10 mA/cm$^2$ FIG. 17 a graph of cyclic voltammograms of ADH and AldDH-based anodes with tethered NAD+/NADH in absence of glycerol, blank solution (black curve) [blank solution: 0.1M KCl in 0.1M phosphate buffer, pH 7.5] and in presence of glycerol ([solution: 0.1M glycerol, 0.1M KCl in 0.1M phosphate buffer, pH 7.5]) where the oxidation peak is at approximately 0.2V and 10 mA/cm$^2$
Figure 17:
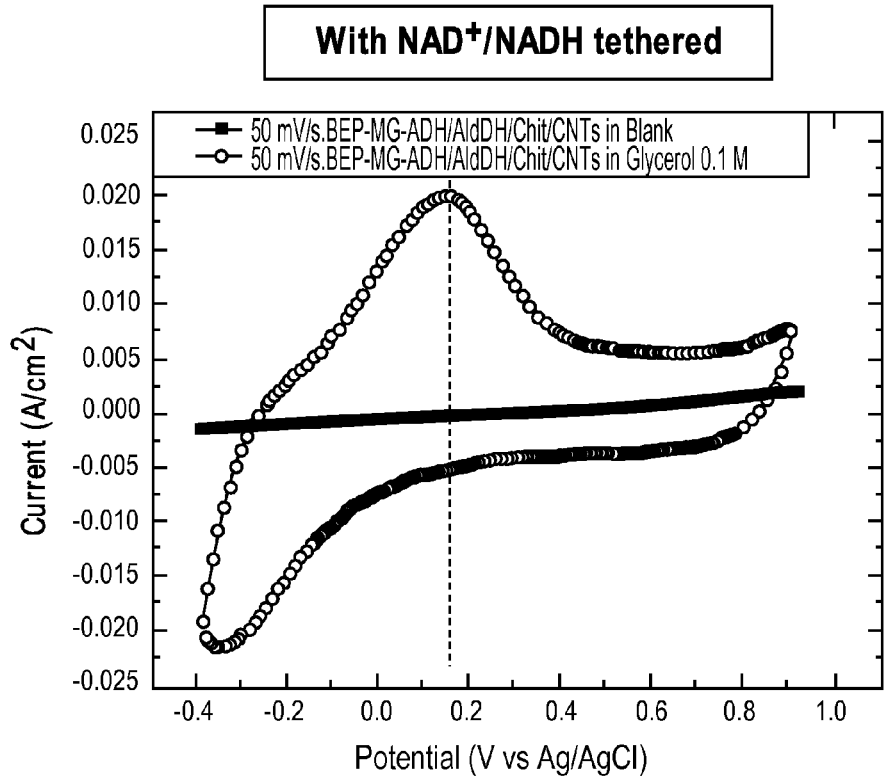

Turning to FIGS. 16 and 17, which show ADH-AldDH-based anodes with NAD in solution and tethered $NAD^+$, respectively, it can be seen that the oxidation peak in the enzymatic system integrating the ADH-AldDH bioanode with $NAD^+/NADH$ in solution shows at ~0.2V and 10 mA/$cm^2$ and the ADH-AldDH with tethered $NAD^+/NADH$ shows at ~0.18V and 20 mA/$cm^2$.

Figure 18:
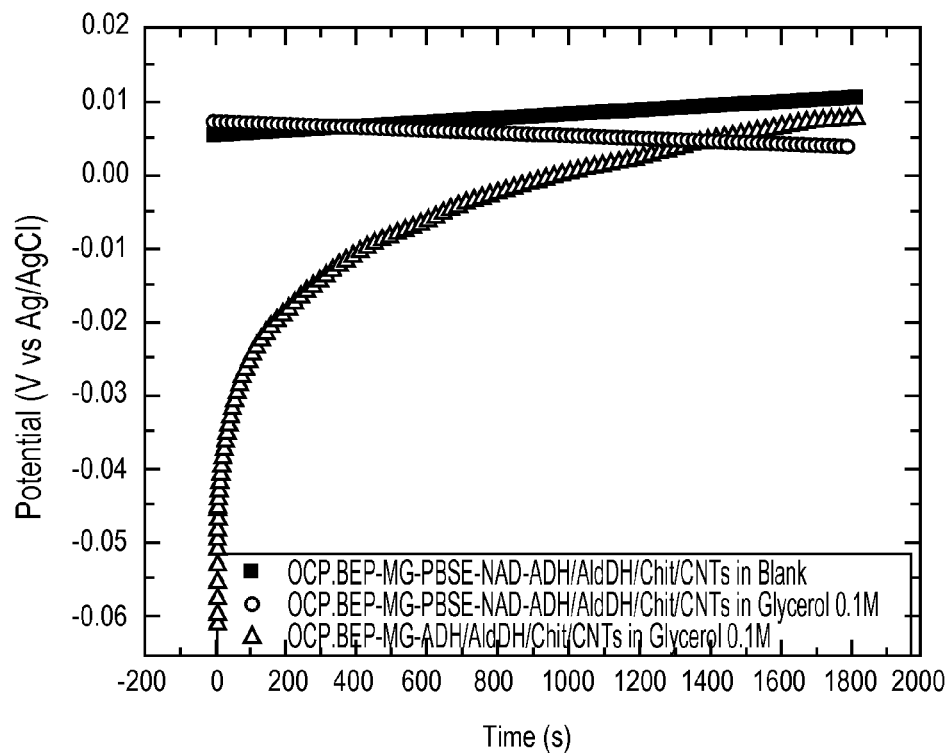
FIG. 18 is a graph showing the open circuit potential of ADH and AldDH-based anodes with NAD tethered in blank solution (black curve) and glycerol 0.1M solution (red curve) [blank solution: 0.1M KCl in 0.1M phosphate buffer, pH 7.5] and NAD in solution with glycerol (blue curve) [solution: 0.1M glycerol, 1 mM NAD+, KCl 0.1M in 0.1M phosphate buffer, pH 7.5]
Figure 19:
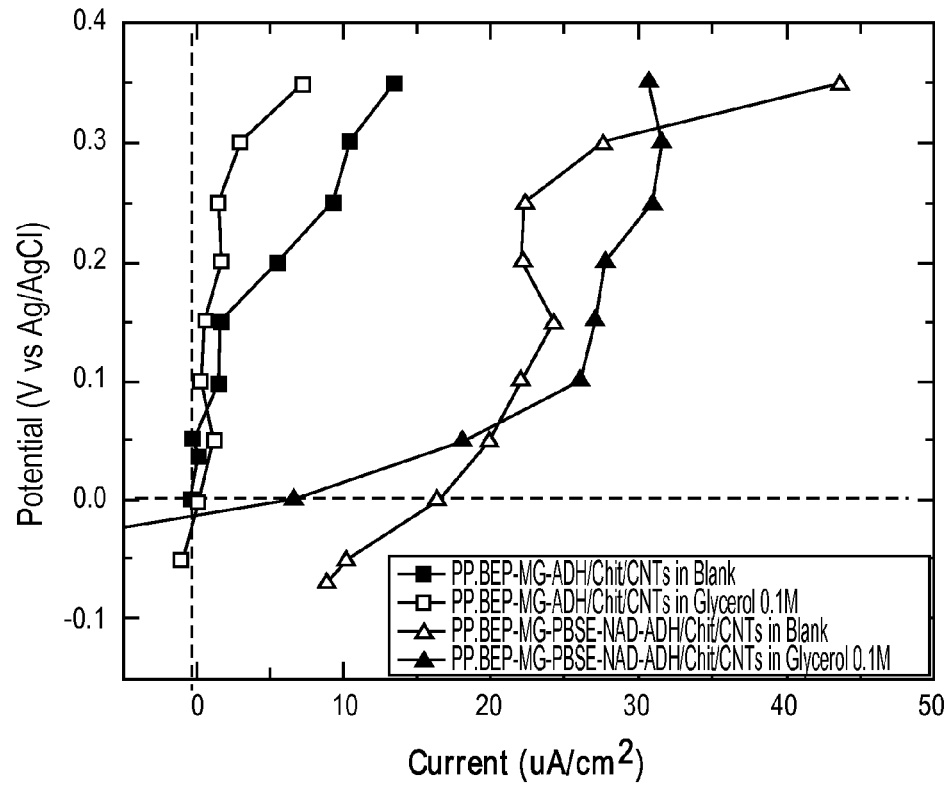
FIG. 19 is a graph showing potentiostatic polarization curves, current densities as a function of potential, of bioanodes employing ADH with NAD in solution in absence ( ) and presence of 0.1 M glycerol ( ) [blank solution: 1 mM NAD+, 0.1M KCl in 0.1M phosphate buffer, pH 7.5; glycerol solution: 0.1M glycerol added to blank solution] and NAD+-tethered, also, in absence ( ) and presence of glycerol 0.1M ( ) [blank: 0.1M KCl in phosphate buffer, pH7.5; glycerol solution: 0.1M glycerol added to blank solution].

Similarly, the ADH and AldDH-based bioanodes with $NAD^+/NADH$ tethered (red curve) on the electrode has improved open circuit potential than the system with $NAD^+/NADH$ in solution (blue curve), $OPC_{Tethered\ NAD+/NADH} < OCP_{NAD+/NADH\ solution}$, (FIG. 18). The electrode with $NAD^+/NADH$ tethered ( ) shows improved current density generation for glycerol oxidation compared to the system with $NAD^+/NADH$ in solution ( ) Also, when the potential is above 50 mV, the tethered $NAD^+$-system shows better performance for current generation ( ) approximately 28 µA/$cm^2$ at 0.1V, compared to ~1.2 µA/$cm^2$ (FIG. 19).

Figure 20:
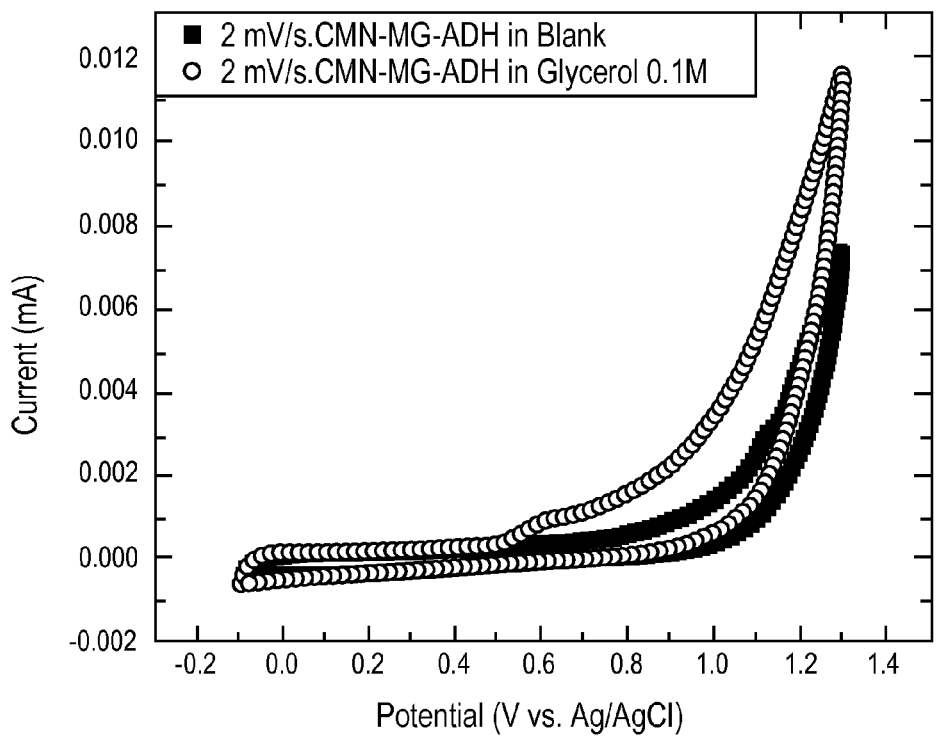
FIG. 20 shows cyclic voltammetries at 2 mV·s$^{-1}$ of CMN-MG-ADH with cofactor in solution in absence (black curve) [blank solution: 1 mM NAD+, 0.1M KCl in 0.1M phosphate buffer, pH 7.5] and presence of glycerol (red curve) [solution: 0.1M glycerol, 1 mM NAD+, 0.1M KCl in 0.1M phosphate buffer, pH 7.5].
Figure 21:
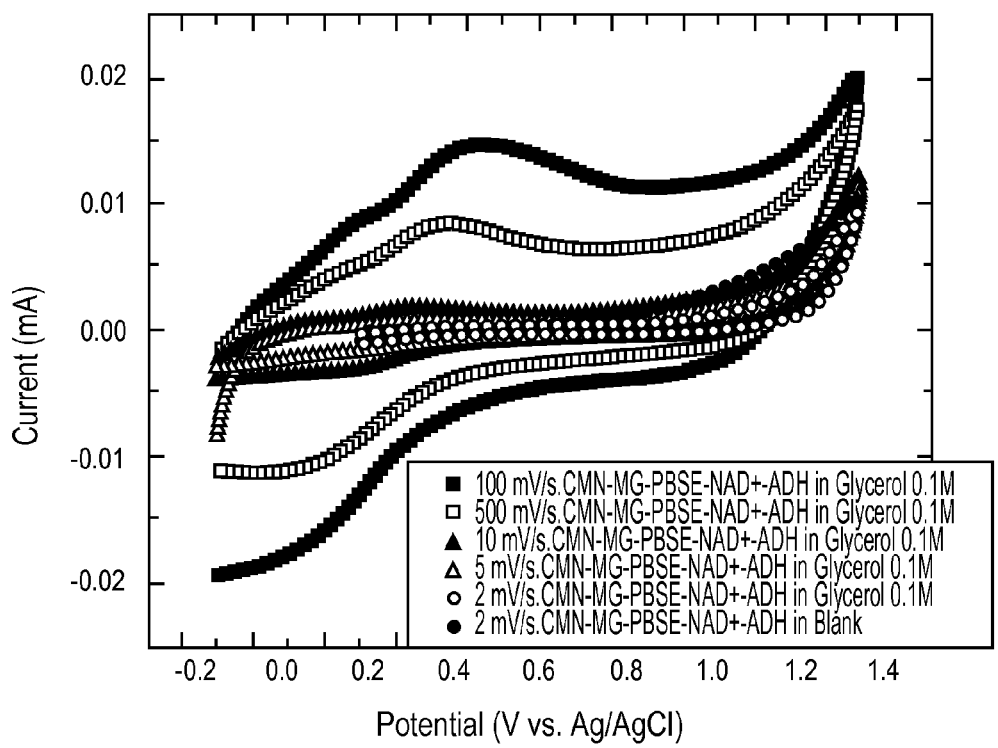
FIG. 21 shows Cyclic voltammetries at different scans rates (2, 5, 10, 50, 100 mV·s$^{-1}$) on CMN-MG-PBSE-NAD+-ADH in blank solution (KCl 0.1M in PB 0.1M, pH7.5) and glycerol 0.1M (in KCl 0.1M in PB 0.1M, pH7.5). Increase in scan rate shows a shift of the oxidation peak to the right.

FIGS. 20 and 21 show the results of similar tests employing an ADH-based electrode integrating CMN-grade bucky paper.

What is claimed is:

1. A complex formed from a NAD/(P)+/NAD(P)H cofactor tethered to a graphene-like material selected from the group consisting of multi-walled carbon nanotubes, single walled carbon nanotubes, graphene, rGO, and other graphene-based or graphene-containing substrates, wherein the cofactor is attached, via a covalent bond, to a pyrene butanoic acid succinimidyl ester tethering molecule which is attached to the graphene-like material via π-π stacking.

2. The complex of claim 1 wherein the graphene-like material is a multi-walled carbon nanotube (MWCNT).

3. The complex of claim 1 further comprising a protein which requires the presence of the cofactor for biological function tethered to the graphene-like material.

4. The complex of claim 3 wherein the protein is an enzyme.

5. The complex of claim 3 wherein the protein is a biocatalyst.

6. A method for forming a biological complex comprising:

covalently attaching a NAD(P)+/NAD(P)H cofactor to a pyrene butanoic acid succinimidyl ester tethering enzyme and;

attaching the tethering enzyme to a graphene-like material selected from the group consisting of multi-walled carbon nanotubes, single walled carbon nanotubes, graphene, rGO, and other graphene-based or graphene-containing substrates via π-π stacking.

7. The method of claim 6 further comprising tethering a protein that interacts with the NAD(P)+/NAD(P)H confactor to the graphene-like material.

8. The method of claim 7 wherein the protein is an enzyme.

9. The method of claim 7 wherein the protein is a biocatalyst.

\* \* \* \* \*